United States Patent [19]

Leppard

[11] Patent Number: 5,059,515

[45] Date of Patent: Oct. 22, 1991

[54] STABILIZERS FOR COLOR PHOTOGRAPHIC RECORDING MATERIALS

[75] Inventor: David G. Leppard, Marly, Switzerland

[73] Assignee: Ciba-Geigy AG, Basel, Switzerland

[21] Appl. No.: 590,038

[22] Filed: Sep. 28, 1990

Related U.S. Application Data

[63] Continuation of Ser. No. 250,850, Sep. 28, 1988, abandoned.

[30] Foreign Application Priority Data

Sep. 28, 1987 [CH] Switzerland .................. 3751/87

[51] Int. Cl.$^5$ .............................. G03C 1/34
[52] U.S. Cl. ....................... 430/551; 430/372; 430/607; 430/610
[58] Field of Search ............. 430/551, 607, 372, 610

[56] References Cited

U.S. PATENT DOCUMENTS

| | | | |
|---|---|---|---|
| 3,247,240 | 4/1966 | Meier et al. ................ | 560/75 |
| 3,644,482 | 2/1972 | Dexter et al. .............. | 560/75 |
| 4,484,000 | 11/1984 | Howell ..................... | 560/75 |
| 4,496,649 | 1/1985 | Leppard et al. ............ | 430/372 |
| 4,526,864 | 7/1985 | Takada et al. ............. | 430/551 |
| 4,549,015 | 10/1985 | Howell ..................... | 544/87 |
| 4,661,601 | 4/1987 | Howell ..................... | 548/251 |
| 4,741,980 | 5/1988 | Kaneko ..................... | 430/17 |
| 4,904,815 | 2/1990 | Howell ..................... | 560/75 |

FOREIGN PATENT DOCUMENTS

| | | |
|---|---|---|
| 0098241 | 1/1984 | European Pat. Off. . |
| 0106799 | 4/1984 | European Pat. Off. . |
| 0216598 | 4/1987 | European Pat. Off. . |
| 0071638 | 6/1975 | Japan . |
| 1056347 | 3/1986 | Japan .................. 430/551 |
| 2172359 | 7/1987 | Japan .................. 430/551 |

OTHER PUBLICATIONS

Research Disclosure No. 27248 (1986) Dec., pp. 733–734.

Primary Examiner—Charles L. Bowers, Jr.
Assistant Examiner—Lee C. Wright
Attorney, Agent, or Firm—Wenderoth, Lind & Ponack

[57] ABSTRACT

Compounds of the formula I or II

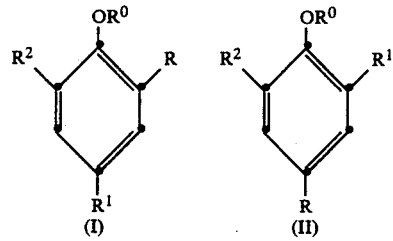

in which R, $R^0$, $R^1$ and $R^2$ are as defined in claim 1.

The compounds, some of which are novel, are light stabilizers for color photographic recording materials.

2 Claims, No Drawings

STABILIZERS FOR COLOR PHOTOGRAPHIC RECORDING MATERIALS

This application is a continuation application of now abandoned application Ser. No. 250,850, filed Sept. 28, 1988, now abandoned.

The present invention relates to the stabilization to light of colour photographic recording materials containing at least one blue-green (cyan), purple (magenta) or yellow coupler, by the addition of a stabilizer to the photographic layer.

It is known to use alkyl-substituted phenols as stabilizers. Thus a large number of alkyl-substituted phenols which act as antioxidants in polymers and oils were described, for example, in EP-A 0,106,799. It was mentioned there that the stabilizers can also be used in photographic systems. However, no reference is made to the fact that these phenols are capable of protecting photographic dyes effectively.

It is also known to use dihydroxyphenyl derivatives in photographic systems as stabilizers or couplers; see, for example, EP-A 069,068, EP-A 069,066 and EP-A 098,241. For example, functionally alkylated hydroquinone ethers are described in EP-A 098,241 as effective stabilizers for photographic dyes.

There still remains, however, interest in improvements in the fastness to light of photographic dyes.

It has now been found that a specific group of phenols and phenol derivatives exhibits an unexpectedly good stabilizing action in a dye layer of photographic recording materials.

The present invention therefore relates to a colour photographic recording material containing at least one blue-green (cyan), purple (magenta) or yellow coupler, which contains, as the stabilizer, at least one compound of the formula I or II

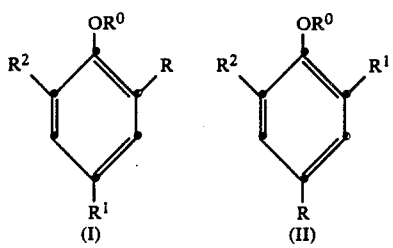

in which R is a group of the formula III or IV

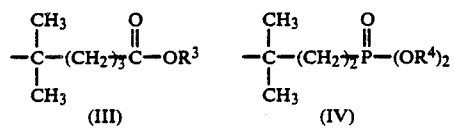

$R^1$ is hydrogen, $C_1$-$C_8$alkyl, cyclohexyl, phenyl-$C_1$-$C_4$alkyl or a group of the formula III or IV, and $R^2$ is as defined for $R^1$, subject to the condition that $R^1$ and $R^2$ cannot simultaneously be hydrogen in the formula II, or $R^2$ is a group of the formula

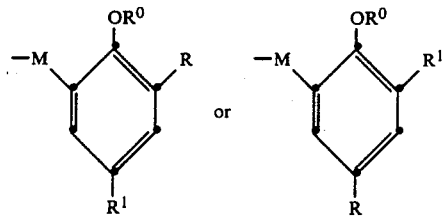

in which M is a direct bond, —$CH_2$— or —S—, $R^3$ is $C_1$-$C_{20}$alkyl which is unsubstituted or substituted by —OH, —$OCOR^5$ or —$OR^5$ and/or which can be interrupted by one or more O atoms, $C_2$-$C_{18}$alkenyl, $C_5$-$C_{12}$cycloalkyl, a phenyl or naphthyl group which is unsubstituted or substituted by one or two alkyl groups, or is phenyl-$C_1$-$C_4$alkyl, a radical ⓧ— or ⓧ—$CH_2$—in which ⓧ—is a 5-membered or 6-membered heterocyclic structure which contains O and which is unsubstituted or substituted by one or two $C_1$-$C_4$alkyl groups, or is a group of the formula V or VI

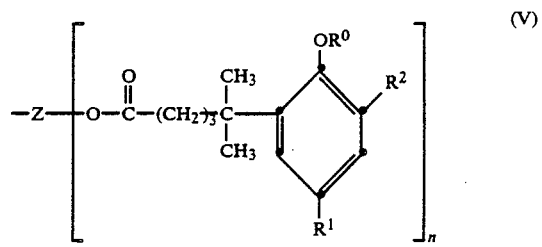

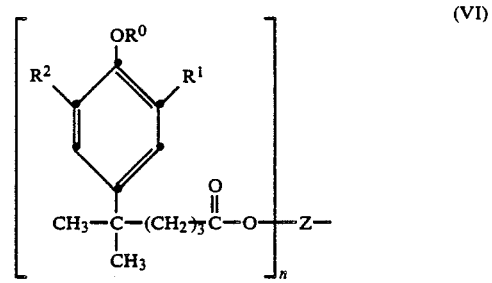

in which n is a number from 1 to 3 and Z is a $C_2$-$C_{18}$alkyl radical which has 2 to 4 valencies and can be interrupted by one or more O and/or S atoms, $R^4$ is $C_1$-$C_{12}$alkyl, $R^5$ is $C_1$-$C^{20}$alkyl, $C_2$-$C_{18}$alkenyl, $C_5C_{12}$cycloalkyl, a phenyl or naphthyl group which is unsubstituted or substituted by one or two alkyl groups, or is phenyl-$C_1$-$C_4$alkyl, $R^0$ is hydrogen, —CO—$R^5$, —$SO_2$—$R^6$, —$COOR^3$, —CO—$COOR^3$, —Si($R^7$, ($R^8$)($R^9$) or a group of the formula VII, VIII or IX

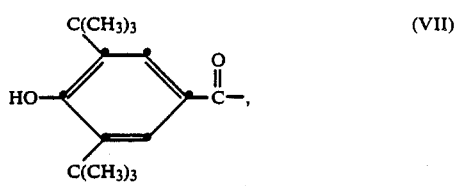

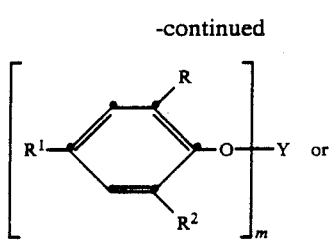

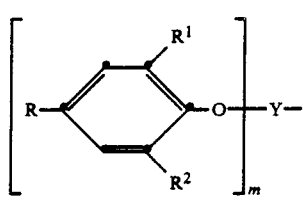

in which m is the number 1 or 2 and Y is $-Si(R^7)(R^8)$ if m is 1 and is $>P$ if m is 2, $R^6$ is $C_1-C_4$alkyl, phenyl or tolyl and $R^7$, $R^8$ and $R^9$ independently of one another are $C_1-C_4$alkyl, phenyl or benzyl.

Examples of $R^1$ and $R^2$ as $C_1-C_8$alkyl are methyl, ethyl, n-propyl, isopropyl, n-butyl, sec-butyl, t-butyl, n-pentyl, t-amyl, n-octyl or 1,1,3,3-tetramethylbutyl.

In addition to the meanings of $R^1$ and $R^2$, $R^4$, as $C_1-C_{12}$alkyl, can be, for example, n-nonyl, n-decyl, 2,7-dimethyloctyl or n-dodecyl.

Examples of $R^3$ and $R^5$ as $C_1-C_{20}$alkyl are methyl, ethyl, n-propyl, isopropyl, n-butyl, sec-butyl, n-pentyl, n-hexyl, n-heptyl, n-octyl, 2-ethylhexyl, n-nonyl, n-decyl, n-dodecyl, n-tetradecyl, n-hexadecyl, n-octadecyl or n-eicosyl.

Examples of $R^4$, $R^6$, $R^7$, $R^8$ and $R^9$ as $C_1-C_4$alkyl are methyl, ethyl, n-propyl, isopropyl, n-butyl, sec-butyl or t-butyl.

Examples of $R^3$ as $C_1-C_{20}$alkyl which can, if appropriate, be interrupted by one or more 0 atoms are 2-methoxyethyl, 2-ethoxyethyl, 2-n-propoxyethyl, 2-n-butoxyethyl,

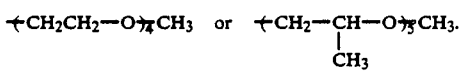

Examples of $R^3$ and $R^5$ as $C_2-C_{18}$alkenyl are vinyl, allyl, n-but-2-enyl, 2-methylprop-2-enyl, n-pent-2-enyl, n-hex-2-enyl, n-hexa-2,4-dienyl, n-dec-9-enyl or n-octadec-17-enyl.

Examples of $R^3$ and $R^5$ as $C_5-C_{12}$cycloalkyl are cyclopentyl, cyclohexyl, cyclooctyl, cyclodecyl, adamantyl or cyclododecyl.

Examples of $R^3$ or $R^5$ as phenyl or naphthyl which is monosubstituted or disubstituted by $C_1-C_4$alkyl are tolyl, xylyl, cumyl, butylphenyl or 2-methylnaphthyl.

Examples of $R^1$, $R^2$, $R^3$ and $R^5$ as phenyl-$C_1-C_4$alkyl are benzyl, phenylethyl, benzylhydryl, naphthylmethyl, -methylbenzyl or , -dimethylbenzyl.

Examples of $R^3$ as $\widehat{X}$— or $\widehat{X}$—$CH_2$— in which $\widehat{X}$ is a 5-membered or 6-membered heterocyclic structure containing 0 are furyl, tetrahydrofuran-2-yl or tetrahydropyran-4-yl. If the heterocyclic structure in $\widehat{X}$—or $\widehat{X}$—$CH_2$— is additionally substituted by one or two $C_1-C_4$alkyl groups, it can be, for example, methylfuryl, 5-methylfurfur-2-yl or 2,6-dimethyltetrahydropyran-4-yl.

Compositions in which $R^0$ is hydrogen and $R^1$ and $R^2$ have a meaning other than hydrogen are preferred.

Compositions which are particularly preferred are those in which $R^3$ in the formula III is a radical of the formula V or VI, n is the number 1 or 3 and, if n=1, Z is $C_2-C_{18}$alkylene which is, if appropriate, interrupted by one or more O atoms and, if n=3, Z is

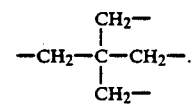

Compositions in which n is the number 3, Z is

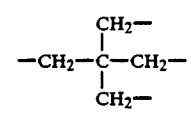

and $R^0$ is hydrogen are very particularly preferred.

Compositions in which $R^0$ has a meaning other than hydrogen, in particular $-CO-R^5$, $-CO-COOR^3$, $-Si(R^7)(R^8)(R^9)$ or a group of the formula VII, VIII or IX are also preferred. $R^3$, $R^4$, $R^7$, $R^8$ and $R^9$ are as defined previously.

Compositions in which $R^0$ is a group of the formula VII

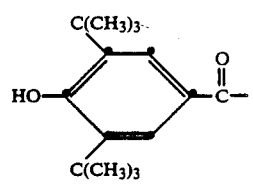

are very particularly preferred.

Compositions in which $R^0$ has a meaning other than hydrogen and $R^3$ in the formula III is a radical of the formula V or VI are also of interest.

The following examples of compounds of the formula I or II in the compositions according to the invention illustrate the invention:

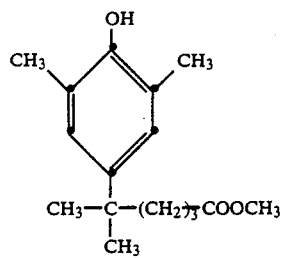
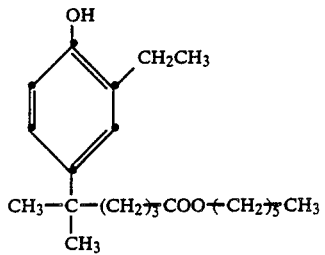
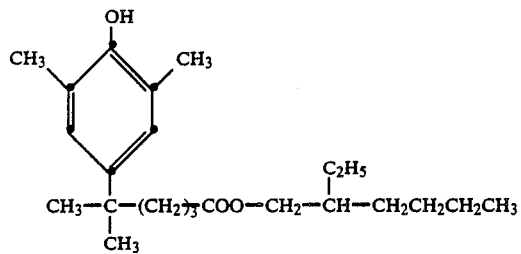
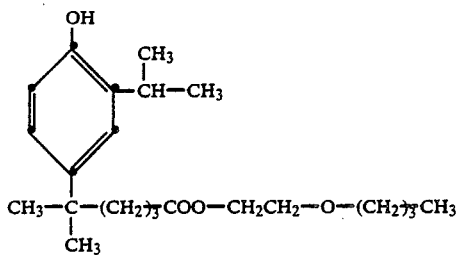
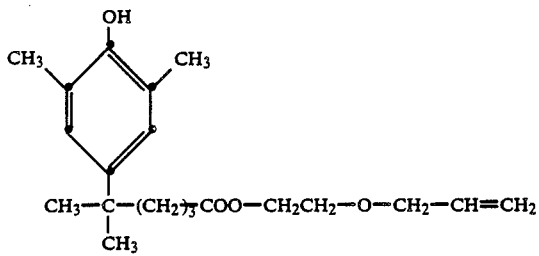
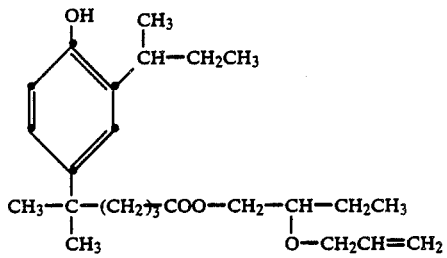

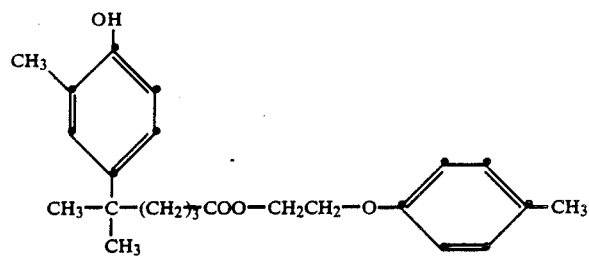
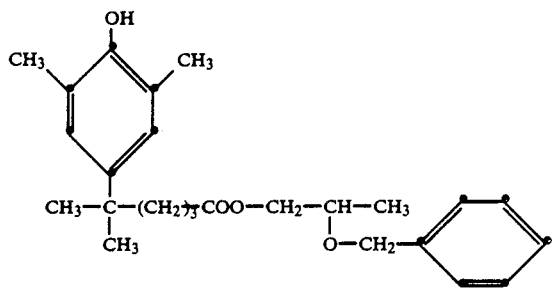
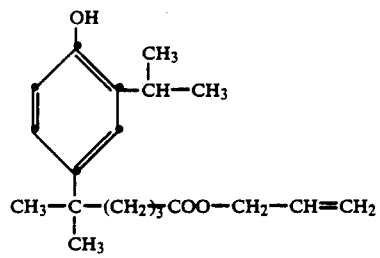
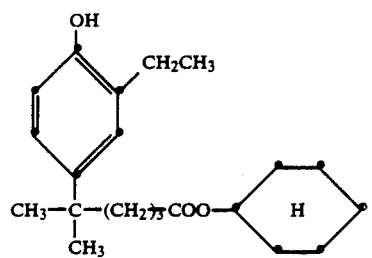
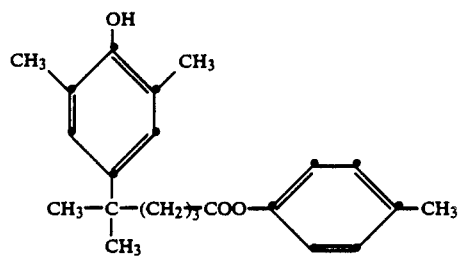
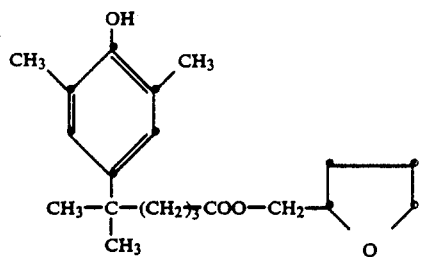

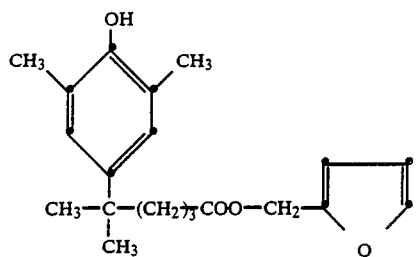
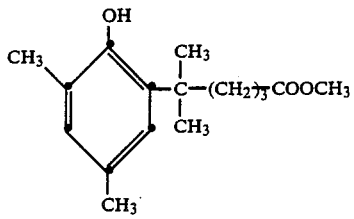
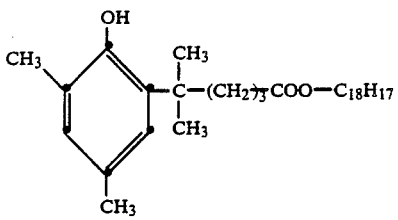
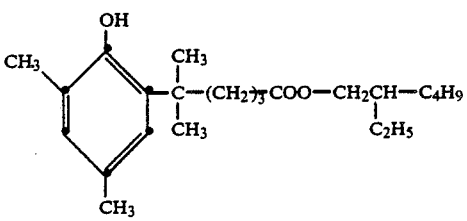
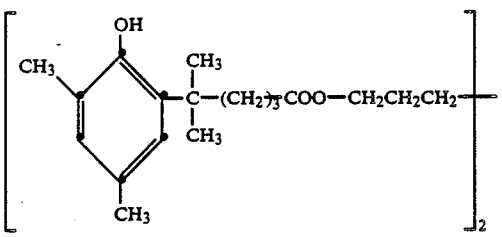
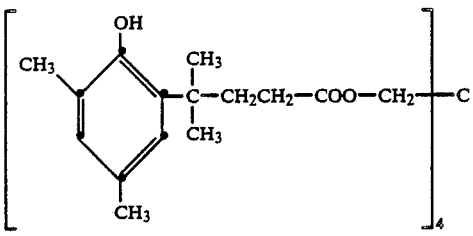
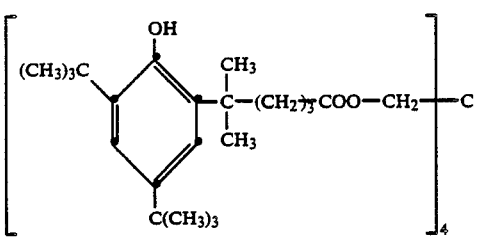

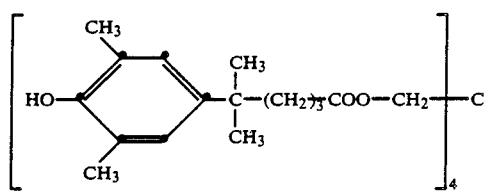
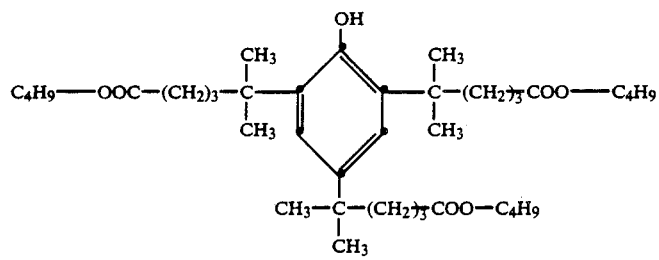
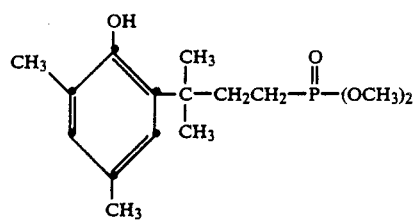
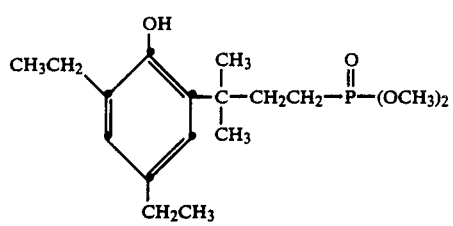
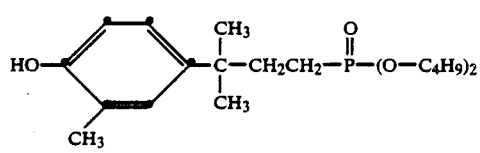
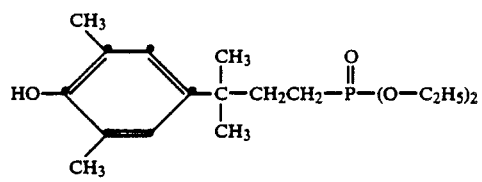
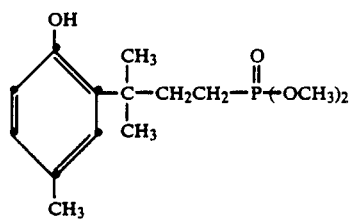

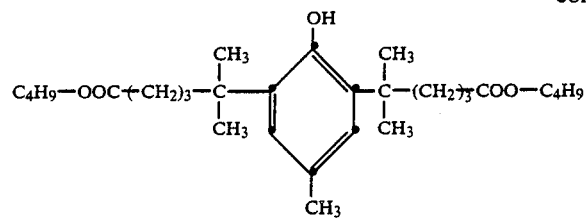
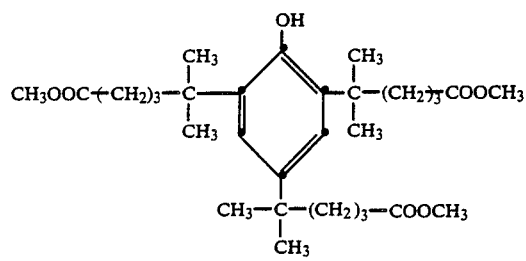
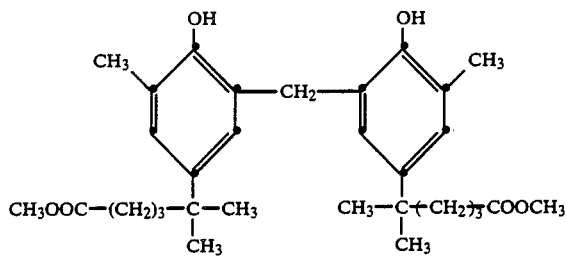
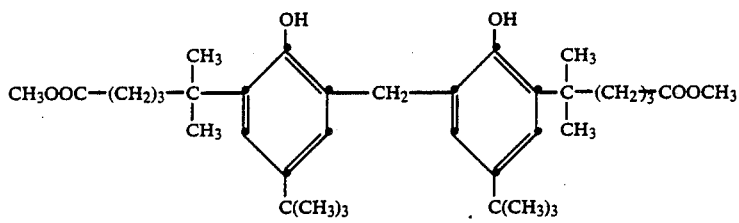
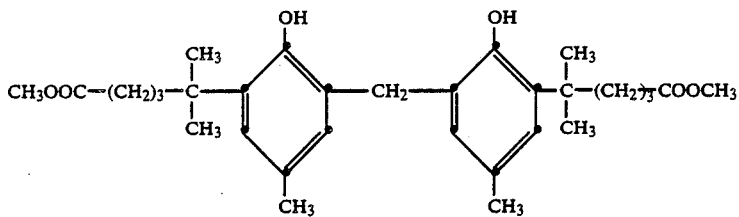
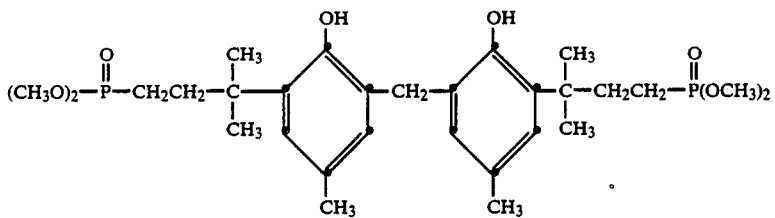
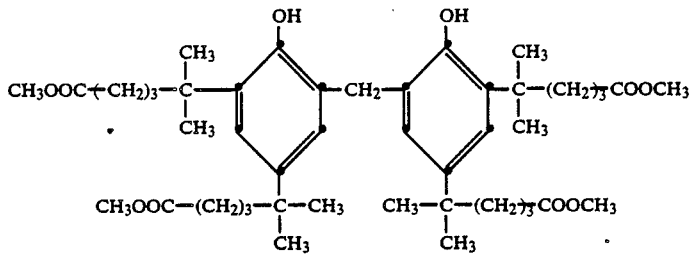

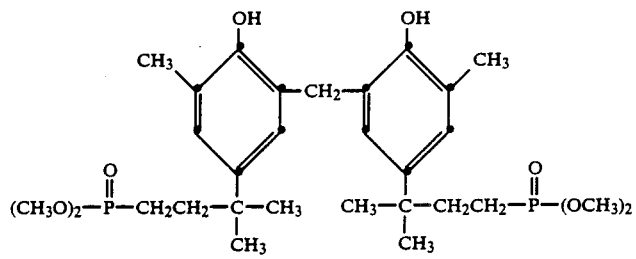
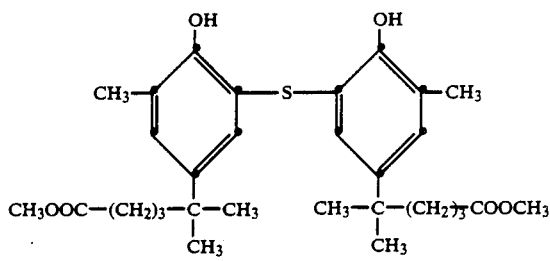
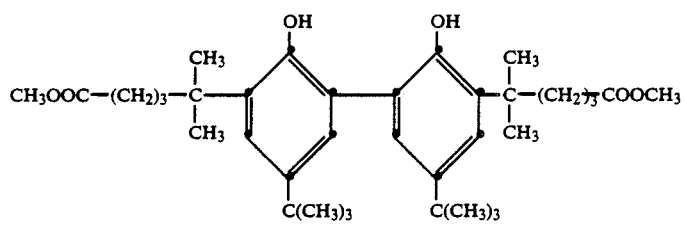
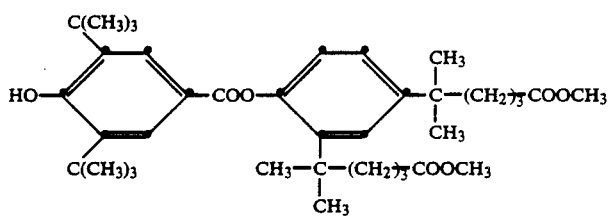
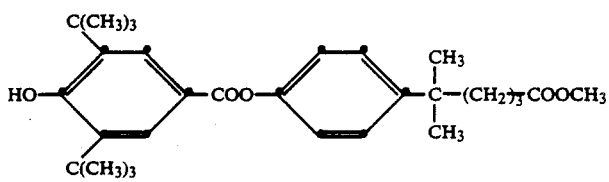
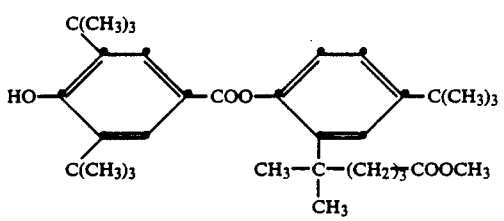
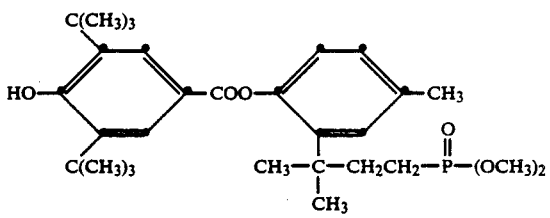

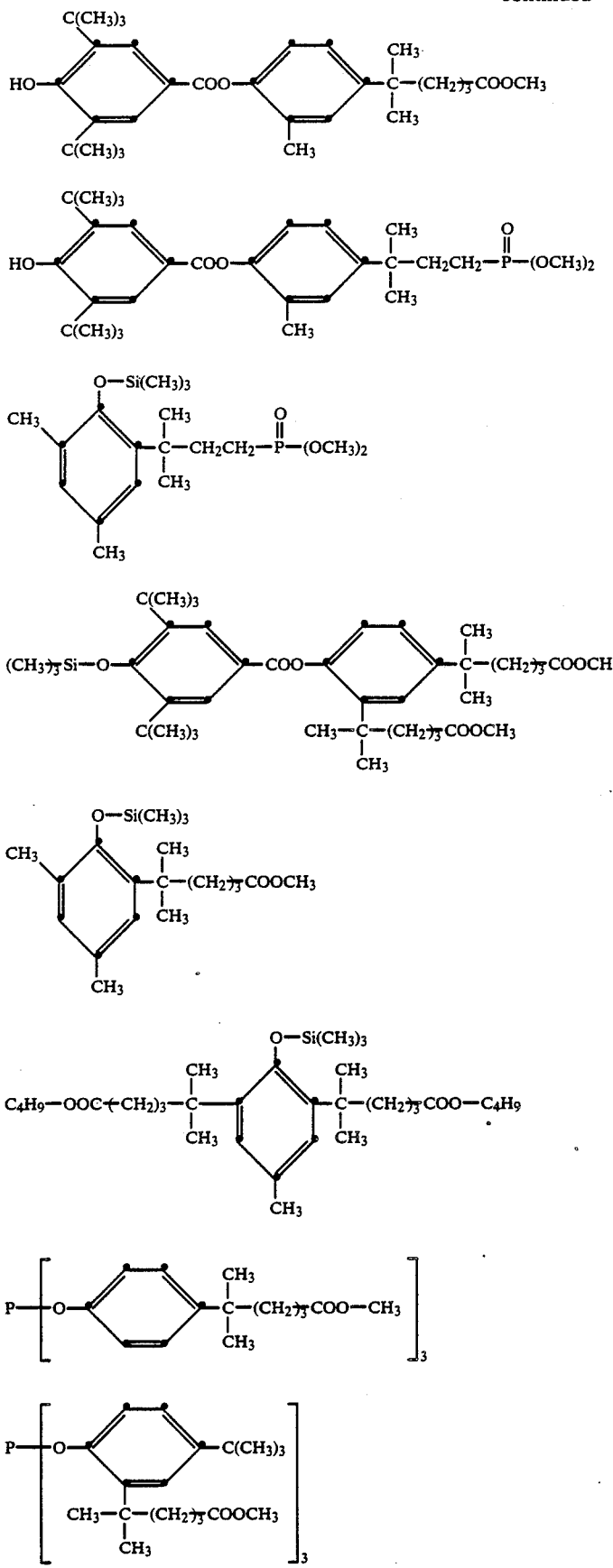

-continued
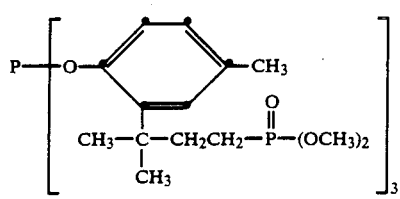
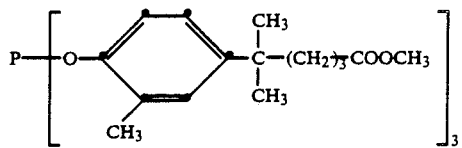
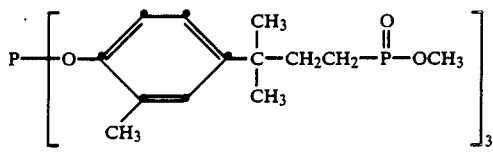
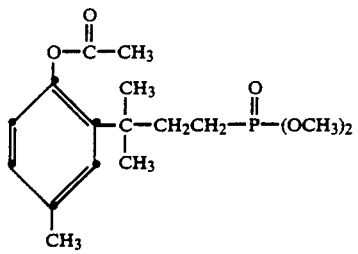
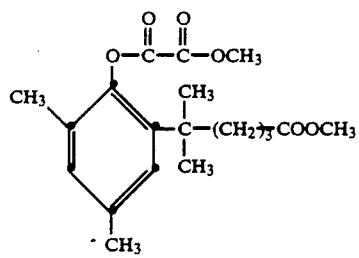
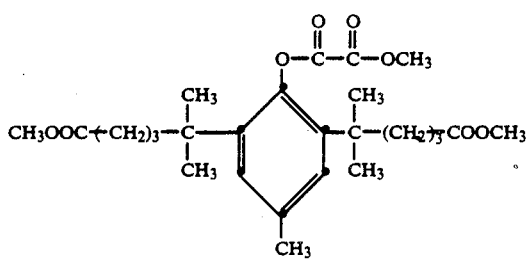
Some of the compounds of the formulae I and II in the compositions according to the invention are novel and are therefore also a subject of the invention.
The invention therefore relates to compounds of the formula Ia or IIa
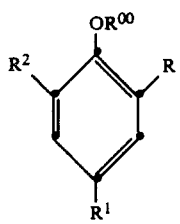
(Ia)
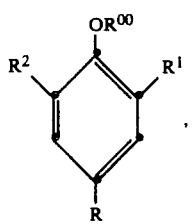
(IIa)

in which $R^{00}$ is as defined above for $R^0$, but in which, in the event that $R^{00}$=H, R is a group of the formula

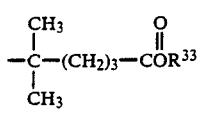

in which $R^{33}$ is a group of the formulae Va or VIa

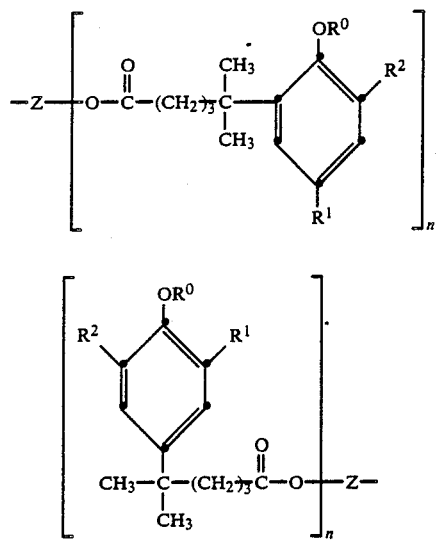

in which n is the number 3, Z is the group

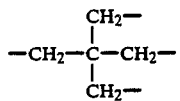

and $R^0$, $R^1$, $R^2$ and R are as defined above.

The possible meanings of R, $R^1$, $R^2$, $R^3$ and $R^0$ which have already been given as examples above under the formulae I and II and are preferred also apply here. Similarly, the data given for $R^0$ also apply analogously to $R^{00}$ in the formulae Ia and IIa.

Compounds of the formula Ia or IIa in which $R^{00}$ is —CO—$R^5$, —CO—COO$R^3$, —Si($R^7$)($R^8$)($R^9$) or a group of the formula VII, VIII or IX, and $R^3$, $R^4$, $R^7$, $R^8$ and $R^9$ are as defined above are preferred.

The compounds of the formula Ia or IIa in which $R^{00}$ is the group of the formula VII

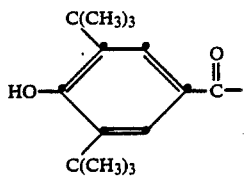

are very particularly preferred.

The preparation of the known and novel compounds of the formulae I, Ia, II and IIa is effected by methods known per se, such as are described, for example, in EP-A 0,106,799.

The novel compounds of the formula Ia or IIa in which $R^{00}$ is other than hydrogen can be prepared, for example, by reacting a phenol of the formulae

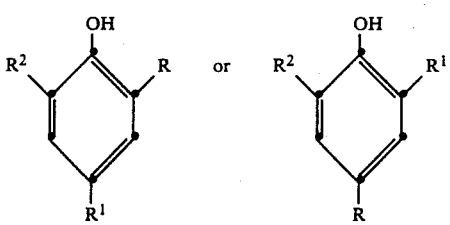

with compounds of the formula $R^{00}$-Hal in which $R^{00}$, R, $R^1$ and $R^2$ are as defined above and Hal is a halogen atom, preferably a chlorine atom, under an atmosphere of nitrogen and, if appropriate, in the presence of a catalyst.

The starting compounds are known compounds and can be prepared by known methods. They are in part also obtainable commercially.

Depending on their structure, the stabilizers according to the invention can be solid-crystalline, waxlike, syrupy or liquid. In some cases they are readily soluble in photographic solvents.

Compositions of the invention containing compounds of the formula I or II which are liquid or readily soluble in photographic solvents are preferred. Those containing liquid compounds of the formula I or II are particularly preferred.

In general, the compositions according to the invention can have a content of 20–1,000 mg/m$^2$, preferably 20–800 mg/m$^2$ and particularly 50–300 mg/m$^2$, of compounds of the formula I or II.

The stabilizers according to the invention are preferably dissolved in an organic solvent or mixture of solvents, and the solution is emulsified in a gelatine solution which is then added to the photographic gelatine layer when the latter is prepared in the form of a dispersion or emulsion. The solvent used is preferably a mixture of a low-boiling and a high-boiling solvent, and the low-boiling solvent is removed during emulsification. Examples of low-boiling solvents which can be used are methyl acetate, ethyl acetate, carbon tetrachloride, methylene dichloride, chloroform, methanol, ethanol, dioxane, acetone or benzene. Examples of high-boiling solvents are dimethylformamide, dimethyl sulphoxide, dialkyl phthalates or triaryl phosphates.

The amount of high-boiling solvent is advantageously within the range from 0.1 to 300%, preferably 10 to 100%, relative to the colour coupler.

The dispersion of the stabilizer solution in the gelatine solution can be effected, for example, in a colloid mill or in a homogenizer or by means of ultrasonic sound. It is also possible to add surface-active agents (emulsifiers) in the course of this. Fine dispersion is a requirement for the homogeneous distribution of the stabilizers in the photographic layer.

If the stabilizers according to the invention are liquid, they can themselves act as photographic solvents. They can be dispersed without further treatment. It is a requirement in this that the stabilizers should be so free-flowing that they have the properties of known photographic solvents, for example of di-n-butyl phthalate or tricresol phosphate.

The stabilizers of the formulae I and II and also the novel stabilizers according to the invention can be added to one or two or all three of the colour-sensitive layers. The sensitized silver halide and the particular colour coupler are present in the layers. The layers can also contain further stabilizers and/or other additives.

The yellow couplers are preferably compounds of the formula A

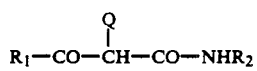

in which $R^1$ is alkyl or aryl, $R^2$ is aryl and Q is hydrogen or a group which can be split off by reaction with the oxidized developer.

One group of yellow couplers is constituted by compounds of the formula A in which $R_1$ is t-butyl and $R_2$ is a group of the formula

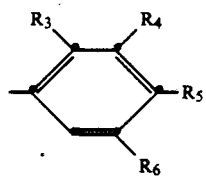

in which $R_3$ is hydrogen, halogen, alkyl or alkoxy and $R_4$, $R_5$ and $R_6$ are hydrogen, halogen, alkyl, alkenyl, alkoxy, aryl, carboxyl, alkoxycarbonyl, a carbamyl group, a sulphonyl or sulphamyl group, or an alkylsulphonamido group, acylamino group, ureido group or amino group.

Preferably, $R_3$ is chlorine, $R_4$ and $R_5$ are hydrogen and $R_6$ is an acylamino group. These also include the compounds of the formula

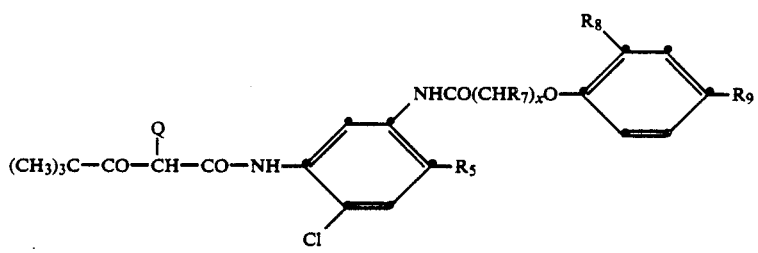

in which x is 0–4, $R_7$ is hydrogen or alkyl and $R_8$ and $R_9$ are alkyl.

Another group of yellow couplers has the formula B

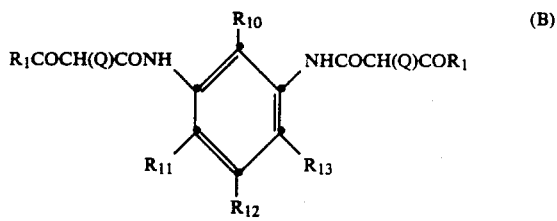

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, a carbamyl group, a sulphone group, sulphamyl group, sulphonamido group, acylamino group, ureido group or amino group and $R_1$ and Q are as defined above.

These include compounds of the formula B in which $R_1$ is t-butyl, $R_{10}$ is chlorine, $R_{11}$ and $R_{13}$ are hydrogen and $R_{12}$ is alkoxycarbonyl.

The detachable group Q in the compounds of the formulae A and B can be hydrogen, halogen, for example Cl, or a group $-OR_{15}$ in which $R_{15}$ is alkyl, aryl, acyl or a heterocyclic radical, or Q is a heterocyclic group

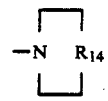

in which $R_{14}$ is an organic divalent group which completes the ring, giving a 4-membered to 7-membered ring.

The compounds of the following formulae are typical examples of customary yellow couplers;

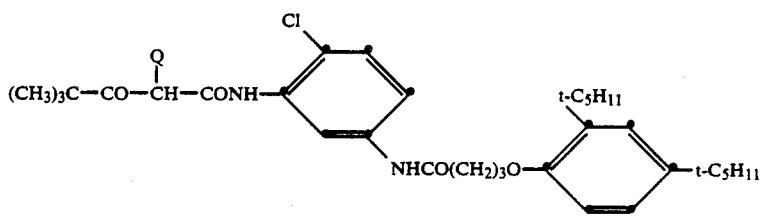

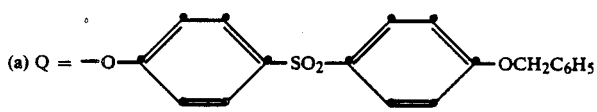

-continued
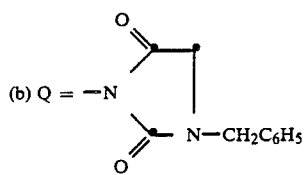
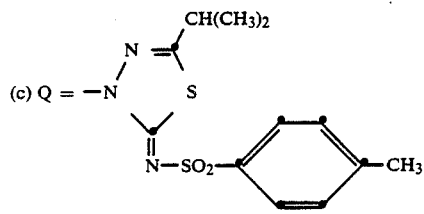
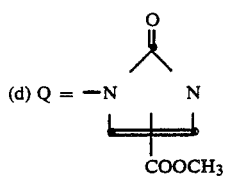
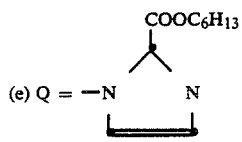
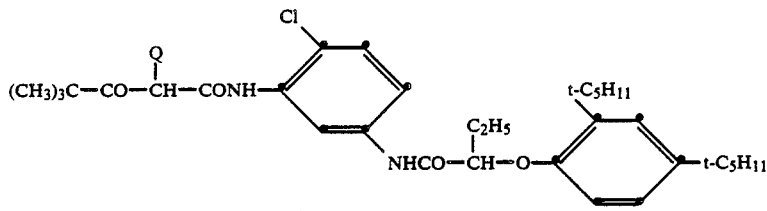
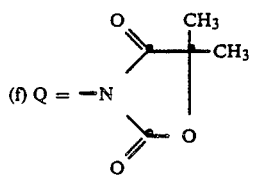
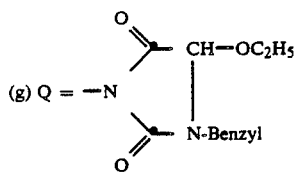
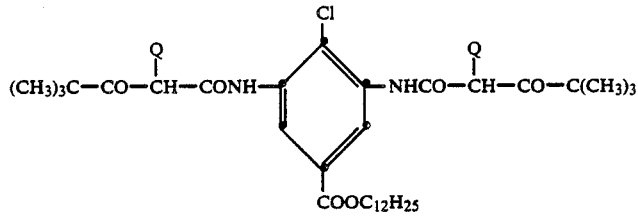

-continued (h) 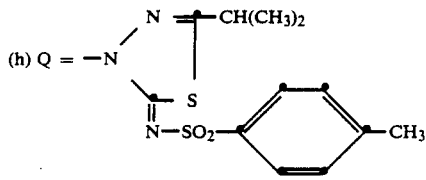

Further examples of yellow couplers can be found in U.S. Pat. Nos. 2,407,210, 2,778,658, 2,875,057, 2,908,513, 2,908,573, 3,227,155, 3,227,550, 2,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752, and 4,022,620, in DE-A 1,547,868, 2,057,941, 2,162,899, 2,163,813, 2,213,461, 2,219,917, 2,261,361, 2,261,362, 2,263,875, 2,329,587, 2,414,006 and 2,422,812 and in GB-A 1,425,020 and 1,077,874.

The yellow couplers are customarily used in an amount of 0.05-2 mol, preferably 0.1-1 mol, per mol of silver halide.

Magenta couplers can, for example, be simple 1-aryl-5-pyrazolones or pyrazole derivatives which are condensed with 5-membered hetero-rings, for example imidazo pyrazoles, pyrazolo pyrazoles, pyrazolo triazoles or pyrazolo tetrazoles.

One group of magenta couplers is constituted by 5-pyrazolones of the formula C

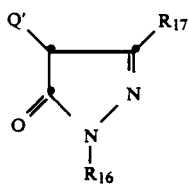 (C)

such as are described in British Patent Specification 2,003,473. In these, $R_{16}$ is hydrogen, alkyl, aryl, alkenyl or a heterocyclic group. $R_{17}$ is hydrogen, alkyl, aryl, a heterocyclic group or an ester group, alkoxy group, alkylthio group, carboxyl group, arylamino group, acylamino group, (thio)urea group, (thio)carbamoyl group, guanidino group or sulphonamido group.

$R_{17}$ is preferably a group

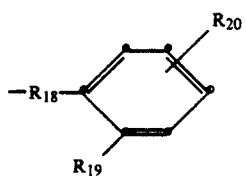

in which $R_{18}$ is imino, acylamino or ureido, $R_{19}$ is hydrogen, halogen, alkyl or alkoxy and $R_{20}$ is hydrogen, alkyl, acylamino, carbamoyl, sulphamoyl, sulphonamido, alkoxycarbonyl, acyloxy or a urethane group.

If Q' is hydrogen, the magenta coupler is tetra-equivalent in respect of the silver halide.

Typical examples of this type of magenta couplers are compounds of the formula

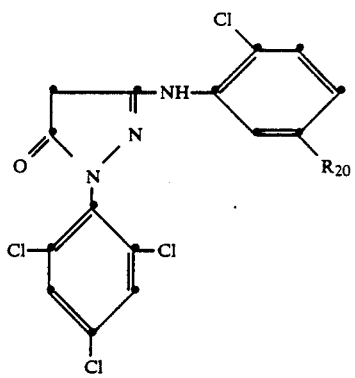

in which $R_{20}$ is as defined above.

Further examples of such tetra-equivalent magenta couplers can be found in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500.

If Q' in formula C is not hydrogen, but a group which is eliminated in the course of the reaction with the oxidized developer, the product is a di-equivalent magenta coupler. In this case, Q can be, for example, halogen or a group which is attached to the pyrazole ring via O, S or N. Di-equivalent couplers of this type produce a higher colour density and are more reactive towards the oxidized developer than are the corresponding tetra-equivalent magenta couplers.

Examples of di-equivalent magenta couplers are described in U.S. Pat. Nos. 3,006,579, 3,419,391, 3,311,476, 3,432,521, 3,214,437, 4,032,346, 3,701,783, 4,351,897 and 3,227,554 and in EP-A 133,503, DE-A 2,944,601 and JP-A 78/34044, 74/53435, 74/53436, 75/53372 and 75/122935.

2 pyrazolone rings can be linked via a divalent Q', and so-called biscouplers are then obtained. Couplers of this type are described, for example, in U.S. Pat. Nos. 2,632,702, U.S. Pat. No. 2,618,864, GB-A 968,461, GB-A 786,859, and JP-A 76/37646, 59/4086, 69/16110, 69/26589, 74/37854 and 74/29638.

Y is preferably an O-alkoxyarylthio group.

As mentioned above, pyrazoles condensed with 5-membered heterocyclic structures—so-called pyrazoloazoles—can also be used as magenta couplers. The advantages of these compared with simple pyrazoles are that they exhibit colours of greater stability to aqueous formaldehyde and purer absorption spectra.

They can be represented by the general formulae $D_1$ and $D_2$

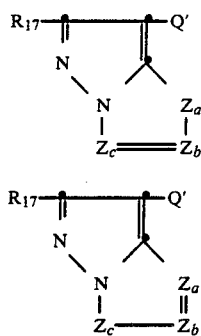

(D₁)

(D₂)

in which $Z_a$, $Z_b$ and $Z_c$ can be the remaining portion of a 5-membered ring which can contain up to 4 nitrogen atoms. The compounds can, accordingly, be pyrazolo-imidazoles, pyrazolo-pyrazoles, pyrazolo-triazoles or pyrazolo-tetrazoles. $R_{17}$ and Q' have the same meanings as in formula C.

Pyrazolo-tetrazoles are described in JP-A 85/33552; pyrazolo-pyrazoles are described in JP-A 85/43,695; pyrazolo-imidazoles are described in JP-A 85/35,732, JP-A 86/18949 and U.S. Pat. No. 4,500,630; and pyrazolo-triazoles are described in JP-A 85/186,567, JP-A 86/47957, JP-A 85/215,687, JP-A 85/197,688, JP-A 85/172,982, EP-A 119,860, EP-A 173,256, EP-A 178,789, EP-A 178,788 and in Research Disclosure 84/24,624.

Further pyrazoloazole magenta couplers are described in JP-A 86/28,947, JP-A 85/140,241, JP-A 85/262,160, JP-A 85/213,937, EP-A 177,765, EP-A 176,804, EP-A 170,164, EP-A 164,130, EP-A 178,794, DE-A 3,516,996, DE-A 3,508,766 and Research Disclosure 81/20,919, 84/24,531 and 85/25,758.

Cyan couplers can be, for example, derivatives of phenol, of 1-naphthol or of pyrazolo quinazolone. Structures of the formula E

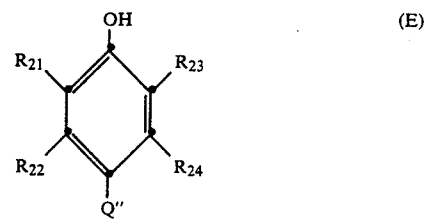

in which $R_{21}$, $R_{22}$, $R_{23}$ and $R_{24}$ are carbamoyl, amido, sulphonamido, phosphoramido or ureido are preferred. $R^{21}$ is preferably H or Cl and $R_{22}$ is preferably an alkyl or amido group. $R_{23}$ is preferably an amido group and $R_{24}$ is preferably hydrogen. Q" is hydrogen or a detachable group which is split off in the course of the reaction with the oxidized developer. A detailed ennumeration of cyan couplers is to be found in U.S. Pat. No. 4,456,681.

The following are examples of customary cyan couplers:

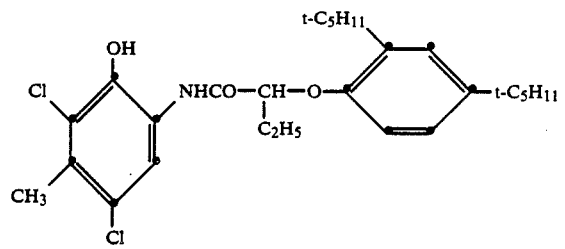

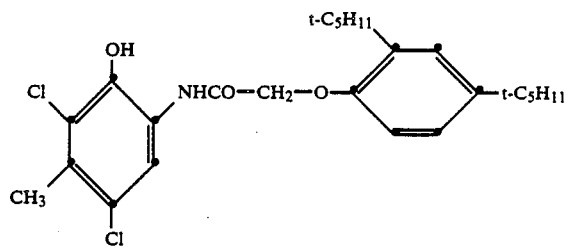

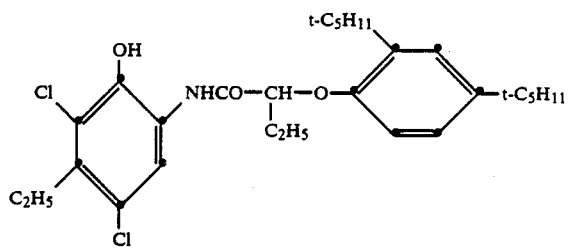

-continued

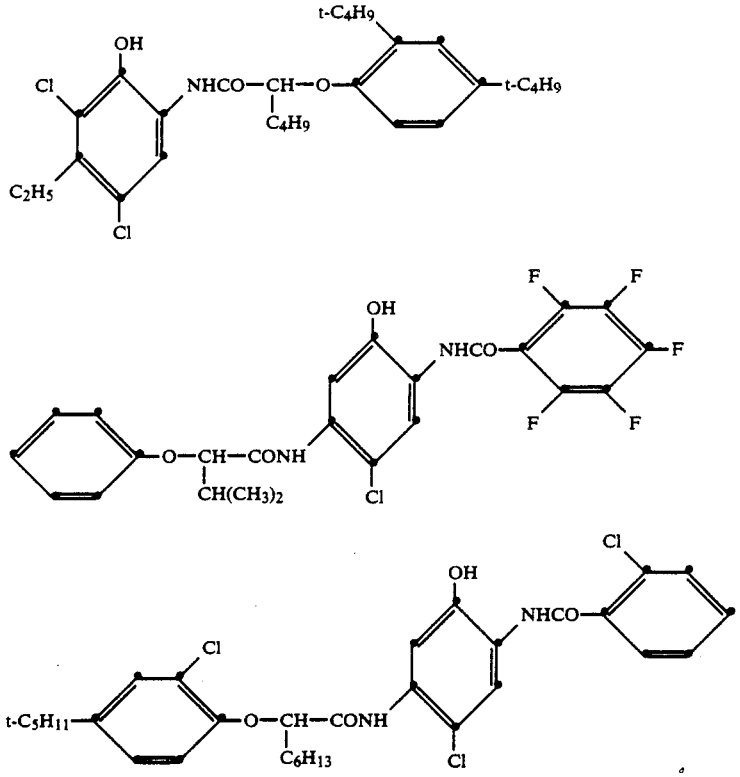

Further examples of cyan couplers are to be found in the following U.S. Pat. Nos.: 2,369,929, 2,423,730, 2,434,272, 2,474,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086 and 4,456,681.

The colour developers customarily used for colour photographic materials are p-dialkylaminoanilines. Examples of these are 4-amino-N,N-diethylaniline, 3-methyl-4-amino-N,N-diethylaniline, 4-amino-N-ethyl-N-α-hydroxyethylanilene, 3-methyl-4-amino-N-ethyl-N-α-hydroxyethylaniline, 3-methyl-4-amino-N-ethyl-N-α-methanesulphonamidoethylaniline, 3-methyl-4-amino-N-ethyl-N-α-methoxyethyl-aniline, 3-α-methanesulphonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α''-methoxyethoxy)-ethoxy]-ethyl-3-methyl-4-aminoaniline, N-ethyl-N-α-(α'-methoxyethoxy)-ethyl-3-methyl-4-aminoaniline and the salts of such compounds, for example sulphates, hydrochlorides or toluene sulphonates.

The stabilizers of the formulae I and II and the novel stabilizers according to the invention can be incorporated into the colour photographic material on their own or together with the colour coupler and, if appropriate, further additives, by dissolving them beforehand in high-boiling organic solvents. It is preferable to use solvents, boiling above 160° C. Typical examples of such solvents are the esters of phthalic acid, phosphoric acid, citric acid, benzoic acid or fatty acids, and also alkylamides and phenols.

In most cases a low-boiling solvent is used in addition in order to facilitate the incorporation of the additives into the colour photographic material. Examples of such solvents are esters, for example ethyl acetate, alcohols, for example butanol, ketones, for example methyl isobutyl ketone, chlorinated hydrocarbons, for example methylene chloride, or amides, for example dimethylformamide. If the additives are themselves liquid, they can also be incorporated into the photographic material without the aid of solvents.

Further details regarding high-boiling solvents which can be used are to be found in the following publications.

Phosphates: GB-A 791,219, BE-A 755,248 and JP-A 76/76739, 78/27449, 78/218,252, 78/97573, 79/148,113, 82/216,177, 82/93323 and 83/216,177.

Phthalates: GB-A 791,219 and JP-A 77/98050, 82/93322, 82/216,176, 82/218,251, 83/24321, 83/45699, and 84/79888.

Amides: GB-A 791,219, JP-A 76/105,043, 77/13600, 77/61089 and 84/189,556, and U.S. Pat. No. 928,741.

Phenols: GB-A 820,329, FR-A 1,200,657 and JP-A 69/69946, 70/3818, 75/123,026, 75/82078, 78/17914, 78/21166, 82/212,114 and 83/45699.

Other oxygen-containing compounds: U.S. Pat. Nos. 3,748,141 and 3,779,765, JP-A 3/75126, 74/101,114, 74/10115, 75/101,625, 76/76740 and 77/61089 and BE-A 826,039.

Other compounds: JP-A 72/115,369, 72/130,258, 73/127,521, 73/76592, 77/13193, 77/36294, 79/95233 and Research Disclosure 82/21918.

The amount of high-boiling solvent is, for example, within the range from 0.1 to 300%, preferably 10 to 100%, relative to the colour coupler.

The photographic emulsions can also contain colour cast inhibitors. These prevent the formation of a colour cast such as are formed, for example, by the coupler reacting with unintentionally oxidized developer or with byproducts of the colour formation process. Such colour cast inhibitors are in most cases hydroquinone derivatives, but can also be derivatives of aminophenols, gallic acid or ascorbic acid. Typical examples of these are to be found in the following publications: U.S. Pat. Nos. 2,360,290, 2,336,327, 2,403,721, 2,418,613, 2,675,314, 2,701,197, 2,704,713, 2,728,659, 2,732,300, and 2,735,365; EP-A 124,877; and JP-A 75/92988, 75/92989, 75/93928, 75/110,337 and 77/146,235.

The photographic emulsions can also contain so-called DIR couplers (Development Inhibitor Release), which produce colourless compounds with the oxidized developer. They are added in order to improve the sharpness and grain of the colour images.

The photographic layers can also contain UV absorbers. These filter out the UV light and thus protect the dyes, the couplers or other components against degradation by light. Examples of such UV absorbers are 2-(2-hydroxyphenyl)-benzotriazoles, 2-hydroxybenzophenones, salicylic acid esters, acrylonitrile derivatives or thiazolines. UV absorbers of this type are illustrated in greater detail in, for example, the following publications: U.S. Pat. Nos. 3,314,794, 3,352,681, 3,705,805, 3,707,375, 4,045,229, 3,700,455, 3,533,794, 3,698,907, 3,705,805 and 3,738,837 and JP-A 71/2784. The 2-(2-hydroxyphenol)-benzotriazoles are the preferred UV absorbers.

The photographic layers can also contain other phenolic compounds which act as a light stabilizer for the colour image and as an agent against colour casts. They can be present, on their own or together with other additives, in a light-sensitive layer (colour layer) or in an intermediate layer. Compounds of this type are described in greater detail in, for example, the following publications:

U.S. Pat. Nos. 3,700,455, 3,591,381, 3,573,052, 4,030,931, 4,174,220, 4,178,184, 4,228,235, 4,279,990, 4,346,165, 4,366,226, 4,447,523, 4,528,264, 4,581,326, 4,562,146 and 4,559,297; GB-A 1,309,277, 1,547,302, 2,023,862, 2,135,788, 2,139,370 and 2,156,091; DE-A 2,301,060, 2,347,708, 2,526,468, 2,621,203 and 3,323,448; DD-A 200,691 and 214,468; EP-A 106,799, 113,124, 125,522, 159,912, 161,577, 164,030, 167,762 and 176,845; JP-A 74/134,326, 76/127,730, 76/30462, 77/3822, 77/154,632, 78/10842, 79/48535, 79/70830, 79/73032, 79/147,038, 79/154,325, 79/155,836, 82/142,638, 83/224,353, 84/5246, 84/72443, 84/87456, 84/192,246, 84/192,247, 84/204,039, 84/204,040, 84/212,837, 84/220,733, 84/222,836, 84/228,249, 86/2540, 86/8843, 86/18835, 86/18836, 87/11456, 87/42245, 87/62157, 86/6652 and Research Disclosure 79/17804.

The photographic layers can also contain certain 'phosphorus-III compounds, in particular phosphites and phosphonites. These act as a light stabilizer for the colour images and as a dark storage stabilizer for magenta couplers. They are preferably added to the high-boiling solvents, together with the coupler. Phosphorus-III compounds of this type are described in greater detail in, for example, the following publications: U.S. Pat. No. 4,407,935, U.S. Pat. No. 4,436,811, EP-A 181,289, JP-A 73/32728, JP-A 76/1420 and JP-A 55/67741.

The photographic layers can also contain organometallic complexes which are light stabilizers for the colour images, in particular for the magenta dyes. Compounds of this type and a combination thereof with other additives are described in greater detail in, for example, the following publications: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165 and 4,590,153; JP-A 81/167,138, 81/168,652, 82/30834 and 82/161,744; EP-A 137,271, 161,577 and 185,506; and DE-A 2,853,865.

The photographic layers can also contain hydroquinone compounds. These act as light stabilizers for the colour coupler and for the colour images and as interceptors of oxidized developer in intermediate layers.

They are used particularly in the magenta layer. Hydroquinone compounds of this type and combinations thereof with other additives are described in greater detail in, for example, the following publications: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572 and 4,559,297; FR-A 885,982; GB-A 891,158, 1,156,167, 1,363,921, 2,022,274, 2,066,975, 2,071,348, 2,081,463, 2,117,526 and 2,156,091; DE-A 2,408,168, 2,726,283, 2,639,930, 2,901,520, 3,308,766, 3,320,483 and 3,323,699; DD-A 216,476, 214,468 and 214,469; EP-A 84,290, 110,214, 115,305, 124,915, 124,877, 144,288, 147,747, 78,165 and 161,577; and JP-A 75/33,733, 75/21,249, 77/128,130, 7/146,234, 79/70,036, 79/133,131, 81/83,742, 81/87,040, 81/109,345, 3/134,628, 82/22,237, 82/112,749, 83/17,431, 83/21,249, 84/75,249, 4/149,348, 84/182,785, 84/180,557, 84/189,342, 84/228,249, 84/101,650, 9/24,019, 79/25,823, 86/48,856, 86/48,857, 86/27,539, 86/6652, 86/72040, 7/11,455, 87/62,157 and Research Disclosure 79/17,901, 79/17,905, 9/18,813, 83/22,827 and 84/24,014.

The photographic layers can also contain derivatives of hydroquinone ethers. These compounds act as light stabilizers and are particularly suitable for stabilizing magenta dyes. Compounds of this type and a combination thereof with other additives are described in greater detail in, for example, the following publications: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,314,011, 4,273,864, 4,264,720, 4,279,990, 4,332,886, 4,436,165, 4,360,589, 4,416,978, 4,385,111, 4,459,015 and 4,559,297; GB-A 1,347,556, 1,366,441, 1,547,392, 1,557,237 and 2,135,788; DE-A 3,214,567; DD 214,469, EP-A 161,577, 67,762, 164,130 and 176,845; and JP-A 76/123,642, 77/35,633, 77/147,433, 78/126, 78/10,430, 78/53,321, 79/24,019, 79/25,823, 79/48,537, 79/44,521, 79/56,833, 79/70,036, 79/70,830, 79/73,032, 79/95,233, 79/145,530, 80/21,004, 80/50,244, 80/52,057, 80/70,840, 80/139,383, 81/30,125, 81/151,936, 82/34,552, 82/68,833, 82/204,036, 82/204,037, 83/134,634, 83/207,039, 84/60,434, 84/101,650, 84/87,450, 84/149,348, 84/182,785, 86/72,040, 87/11,455, 87/62,157, 87/63,149, 86/2151, 86/6652, 86/48,855 and Research Disclosure 78/17,051.

The invention also relates to the use of the compounds, according to the invention, of the formulae Ia and IIa as stabilizers in colour photographic recording materials.

The following examples serve to illustrate the invention further. All the reactions in the preparation examples were carried out under nitrogen. Any percentages given are percentages by weight.

PREPARATION EXAMPLES

Example 1

[2.4-bis-(5'-Methoxycarbonyl-2'-methylpent-2'-yl)-phenyl]4-hydroxy-3,5-di-t-butylbenzoate

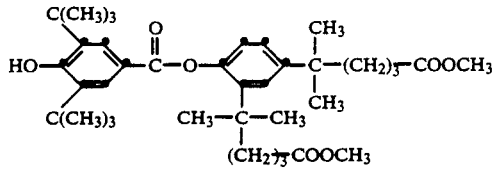

7.5 g of 2,4-bis-(5'-methoxycarbonyl-2'-methylpent-2'-yl)-phenol and 5.4 g of 3,5-di-t-butyl-4-hydroxybenzoyl chloride are heated for 35 hours in 80 ml of boiling toluene. The solvent is then removed under reduced pressure and the residual oil is purified by column chromatography (SiO$_2$; 9:1 toluene:ethyl acetate). 10.1 g of the end product are obtained in the form of a colourless oil.

Example 2

4'-Methyl-2'-[4''-(0,0-dimethylphosphonato)-2''-methylbutyl-]phenyl 4-hydroxy-3,5-di-t-butylbenzoate

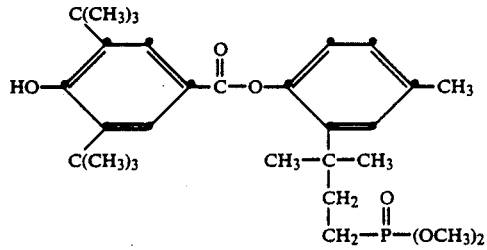

2.86 g of 0,0-dimethyl [3-(2'-hydroxy-5'-methylphenyl)-3-methylbut-1-yl-]-phosphonate and 2.69 g of 4-hydroxy-3,5-di-t-butylbenzoyl chloride are heated for 6 hours in 40 ml of boiling toluene. The reaction mixture is washed and dried and freed from solvent under reduced pressure. The residual oil is then purified by means of column chromatography, as in Example 1. 1.8 g of the end product are obtained in the form of a colourless, viscous oil.

Example 3

0,0-Dimethyl [2'-acetoxy-5'-methylphenyl)-3-methyl-but-1-yl-]-phosphonate

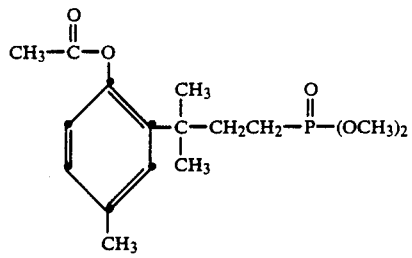

2.86 g of 0,0-dimethyl [3-(2,-hydroxy-5'-methylphenyl)-3-methylbut-1-yl)-phosphonate are dissolved in 30 ml of methylene chloride. 1.9 ml of pyridine are added to the solution and it is then cooled to 0° C. 1.72 g of acetyl chloride in 5 ml of methylene chloride are added dropwise in the course of 15 minutes and the reaction mixture is stirred for 4 hours at room temperature and is then poured into ice water. The organic phase is washed, dried and freed from the solvent under reduced pressure. The residual oil is purified by means of column chromatography, as in Example 1. 1.8 g of the end product are obtained in the form of a yellow oil.

Example 4

0,0-Dimethyl [3-(2'-methoxyoxalyloxy-5'-methylphenyl-3-methyl-but-1-yl]-phosphonate

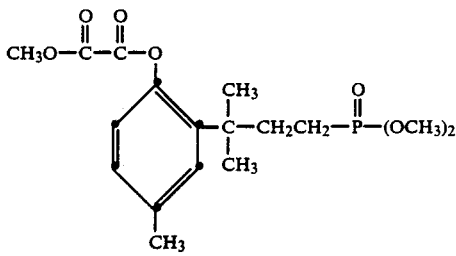

The procedure is as described in Example 3, except that the corresponding amount of oxalic acid monomethyl ester-chloride is employed and the mixture is stirred for 18 hours at room temperature. 3.6 g of the end product are obtained in the for ⓡof a slightly yellow oil.

Example 5

0,0-Dimethyl [3-(5'-methyl-2'-trimethylsiloxyphenyl)-3-methyl-but-1-yl]-phosphonate

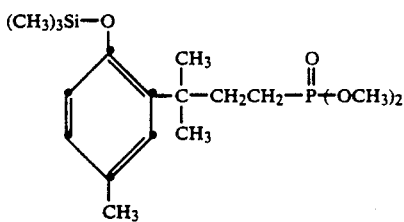

The procedure is as described in Example 3, except that the corresponding amount of trimethylchlorosilane is employed and the mixture is stirred for 18 hours at room temperature. 2.8 g of the end product are obtained in the form of a slightly brown oil.

Example 6

Tris-2-[4'-dimethylphosphonato-2'-methylbut-2-yl)-4-methylphenyl]-phosphite

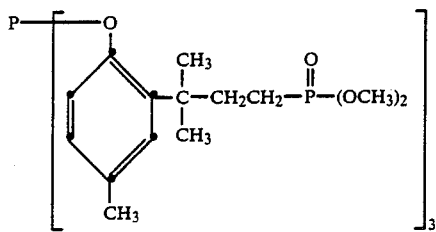

The procedure is as described in Example 3, except that the corresponding amount of phosphorus trichloride is employed and the mixture is boiled under reflux for 24 hours. 1.46 g of the end product are obtained in the form of a colourless oil.

Example 7

4-t-Butyl-2-(5'-methoxycarbonyl-2'-methylpent-2'-yl)-methoxyoxalyloxybenzene

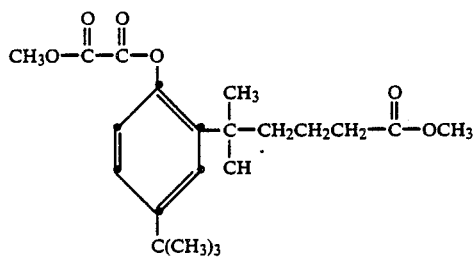

2.9 g of 4-t-butyl-2-(5'-methoxycarbonyl-2'-methylpent-2'-yl)-phenol and 0.95 g of pyridine are dissolved in 20 ml of methylene chloride. The solution is cooled to 0° C. and 1.35 g of oxalic acid monomethyl esterchloride are added dropwise in the course of 10 minutes. The reaction mixture is stirred for 1 hour at room temperature and is then poured into ice water. The organic phase is washed, dried and freed from the solvent under reduced pressure. The residual oil is purified by means of column chromatography (SiO$_2$; 1:5 ethyl acetate: petroleum ether). 3.0 g of the end product are obtained in the form of a slightly yellow oil.

Example 8

2,4-Bis-(5'-methoxycarbonyl-2'-methylpent-2'-yl)-trimethylsilyloxybenzene

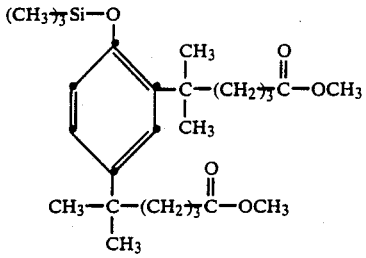

2.0 g of 2,4-bis-(5'-methoxycarbonyl-2'-methylpent-2'-yl)-phenol and 1,04 g of pyridine are dissolved in 20 ml of methylene chloride. The solution is cooled to 0° C. and 1.14 g of trimethylchlorosilane in 10 ml of CH$_2$Cl$_2$ is added dropwise in the course of 10 minutes. The reaction mixture is stirred at room temperature for 90 minutes and is then poured into a mixture of 10% NaHCO$_3$ solution/CH$_2$Cl$_2$/ice. The organic phase is washed, dried and freed from the solvent under reduced pressure. The residual oil is purified by means of column chromatography (SiO$_2$; 1:12 ethyl acetate: hexane) 1.8 g of the end product are obtained in the form of a colourless oil.

Example 9

Pentaerythrityl tetrakis-[5-(2'-methoxyoxalyloxy-3',5'-dimethylphenyl)-5-methylhexanoate]

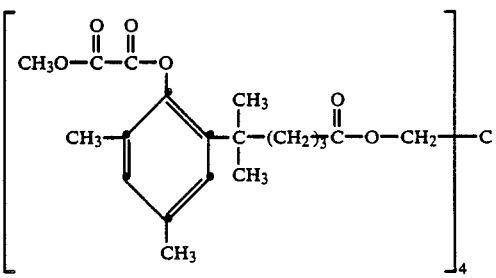

1.07 g of pentaerythrityl tetrakis-[5-(2'-hydroxy-3'-,5'-dimethylphenyl)-5-methylhexanoate] are dissolved in 9 ml of toluene and 1 ml of dimethylformamide. 1.0 g of triethylamine is added to the solution, and the mixture is cooled to 0° C. A solution of 0.98 g of oxalic acid monomethyl ester-chloride in 4.5 ml of toluene and 0.5 ml of dimethylformamide is then added dropwise to the mixture. The resulting reaction mixture is stirred for 24 hours at room temperature and is then poured into ice water. The organic phase is washed, dried and freed from the solvent under reduced pressure. The residual oil is purified by means of column chromatography (SiO$_2$; 1:3 ethyl acetate: petroleum ether). 0.6 g of the end product is obtained in the form of a slightly yellow oil.

Example 10

Pentaerythrityl tetrakis-[5-(2'-trimethylsiloxy-3',5'-dimethylphenyl)-5-methylhexanoate]

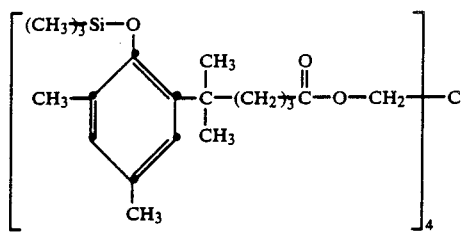

1.0 g of pentaerythrityl tetrakis-[5-(2'-hydroxy-3',5'-dimethylphenyl)-5-methylhexanoate] and 1.19 g of 1,8-diazabicyclo[5.4.0]undec-7-ene (DBU) are dissolved in 20 ml of toluene. The solution is cooled to 0° C. and a solution of 0.63 g of trimethylchlorosilane in 10 ml of toluene is added dropwise.

The reaction mixture is stirred for 18 hours at room temperature and is then poured into a mixture of 10% NaHCO$_3$/ice water. The organic Phase is washed, dried and freed from the solvent under reduced pressure. The residual oil is purified by means of column chromatography (SiO$_2$; 19:1 hexane:ethyl acetate). 0.58 g of the end product is obtained in the form of a colourless, viscous oil.

USE EXAMPLES

Examples 11-15

0.087 g of the yellow coupler of the formula

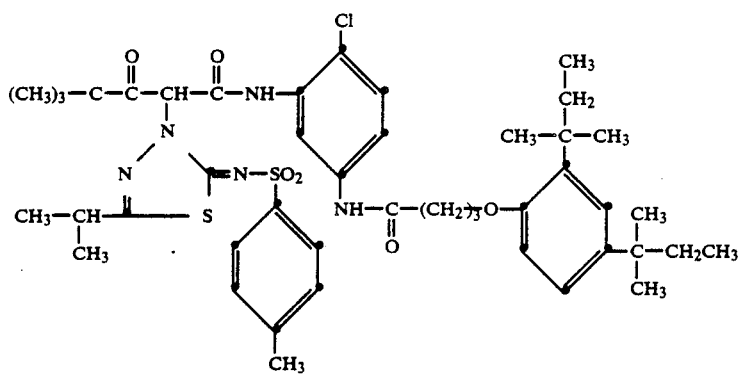

is dissolved in 2.0 ml of a mixture consisting ⓒf a stabilizer of the formula I or II and ethyl acetate (2.25 g/100 ml). 9.0 ml of a 2.3% aqueous solution of gelatine, adjusted to a pH of 6.5, and 1.744 g/l of the wetting agent of the formula

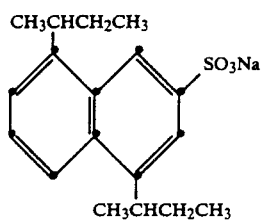

are added to 1.0 ml of this solution. 2 ml of a silver bromide emulsion having a silver content of 6.0 g/l and also 1.0 ml of a 0.7% aqueous solution of the curing agent of the formula

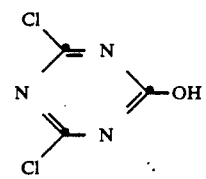

are added to 5.0 ml of the coupler emulsion thus obtained, and the mixture is poured onto a plastic-coated sheet of paper of 13×18 cm. After a curing time of 7 days, the samples are exposed behind a silver step wedge at 125 lux.second and are then processed by the Kodak Ektaprint 2 ® process.

One half of the yellow wedges thus obtained is irradiated at a total of 30K joules/cm$^2$ in an Atlas Weather-Ometer by means of a 2,500 watt xenon lamp, and the other half is irradiated at a total of 60K joules/cm$^2$ in an Atlas Weather Ometer behind a UV filter (Kodak 2C) by means of a 2,500 watt xenon lamp.

A sample with no stabilizer is processed at the same time as a standard.

Table 1 below shows the loss in colour density which takes place during the irradiation at the absorption maximum of the yellow dye, measured by means of a Macbeth TR 924A densitometer.

The light stabilizing effect can be seen from the loss in colour density. The smaller the loss in density, the higher the effectiveness as a light stabilizer.

TABLE 1

| Example | Stabilizer | Loss of colour density, % | |
|---|---|---|---|
| | | 30 K joules/cm$^2$ | 60 K joules/cm$^2$ |
| — | None | 75 | 33 |

TABLE 1-continued

| Example | Stabilizer | Loss of colour density, % 30 K joules/cm² | 60 K joules/cm² |
|---|---|---|---|
| 11 | 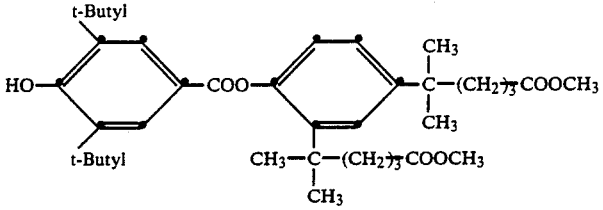 | 34 | 13 |
| 12 | 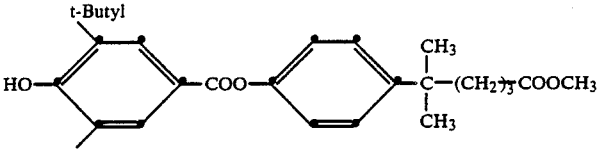 | 33 | 13 |
| 13 | 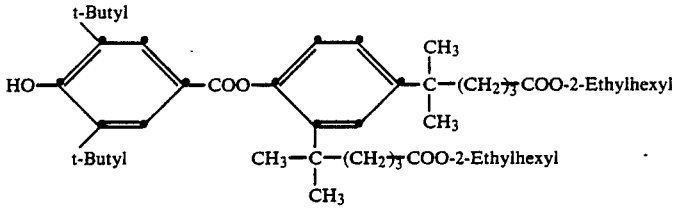 | 36 | 13 |
| 14 | 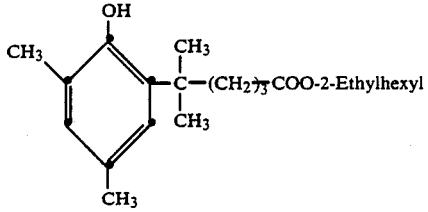 | 47 | 15 |
| 15 | 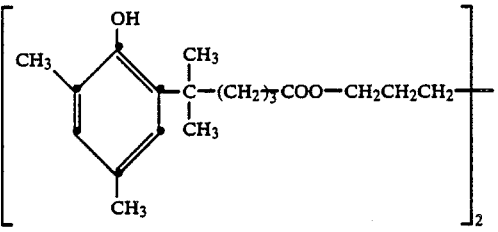 | 25 | 8 |

Examples 16 and 17

0.033 g of the cyan coupler of the formula

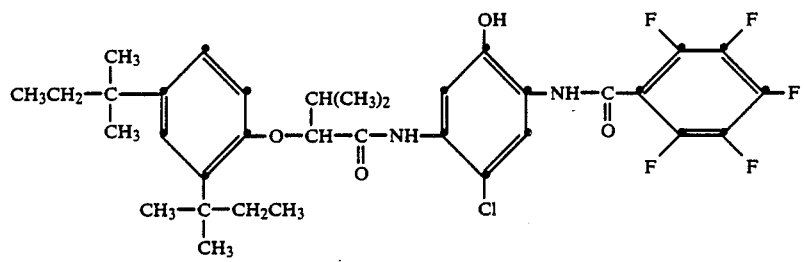

and one of the stabilizers indicated in Table 2 are dissolved in each case in 2.0 ml of a mixture of dibutyl phthalate and ethyl acetate (0.8 g/100 ml).

9.0 ml of a 2.3% aqueous solution of gelatine, adjusted to a pH of 6.5, and 0.872 g/l of the wetting agent from Example 11 are added to 1.0 ml of this solution.

The further processing of the emulsion is as described in Example 11, except that the silver bromide emulsion has a silver content of 3 g/l.

The resulting colour step wedges are irradiated at a total of 30K joules/cm² in an Atlas Weather-Ometer by means of a 2,500 watt xenon lamp, and the loss of colour density is then determined as described in Example 11. A sample with no stabilizer is processed at the same time as a standard.

The results are collated in Table 2 below.

and one of the stabilizers indicated in Table 3 are in each case dissolved in 2.0 ml of a mixture of dibutyl phthalate and ethyl acetate (0.8 g/100 ml).

Further processing is as in Example 16. The resulting colour step wedges are stored in an air-conditioned cabinet for 28 days at 75° C. and 60% relative humidity. The loss of colour density was then determined as de-

TABLE 2

| Example | Stabilizer | Loss of colour density, % at 30 K joule/cm² |
|---|---|---|
| — | None | 44 |
| 16 | HO—(2,6-di-t-Butyl-phenyl)—COO—(4-[C(CH₃)₂(CH₂)₃COOCH₃], 3-[C(CH₃)₂(CH₂)₃COOCH₃]-phenyl) | 37 |
| 17 | HO—(2,6-di-t-Butyl-phenyl)—COO—(4-[C(CH₃)₂(CH₂)₃COOCH₃]-phenyl) | 38 |

Examples 18–23

0.025 g of the cyan coupler of the formula

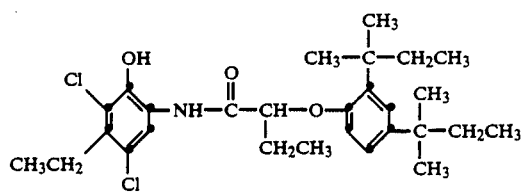

scribed in Example 11.

A sample with no stabilizer is processed at the same time as a standard. The results are collated in Table 3 below.

TABLE 3

| Example | Stabilizer | Loss of colour density, %, after 28 days storage in an air-conditioned cabinet |
|---|---|---|
| — | None | 11 |
| 18 | HO—(2,6-di-t-Butyl-phenyl)—COO—(4-[C(CH₃)₂(CH₂)₃COOCH₃], 3-[C(CH₃)₂(CH₂)₃COOCH₃]-phenyl) | 5 |
| 19 | HO—(2,6-di-t-Butyl-phenyl)—COO—(4-[C(CH₃)₂(CH₂)₃COOCH₃]-phenyl) | 5 |

TABLE 3-continued

| Example | Stabilizer | Loss of colour density, %, after 28 days storage in an air-conditioned cabinet |
|---|---|---|
| 20 | HO–[3,5-di-t-Butyl-phenyl]–COO–[4-CH$_3$-phenyl with 2-C(CH$_3$)$_2$(CH$_2$)$_3$COOCH$_3$] | 6 |
| 21 | HO–[3,5-di-t-Butyl-phenyl]–COO–[3-CH$_3$,4-C(CH$_3$)$_2$(CH$_2$)$_3$COOCH$_3$-phenyl] | 6 |
| 22 | HO–[3,5-di-t-Butyl-phenyl]–COO–[4-CH$_3$-phenyl with 2-CH$_3$-CH(CH$_3$)CH$_2$CH$_2$–P(=O)(OCH$_3$)$_2$] | 6 |
| 23 | 2,4-bis[C(CH$_3$)$_2$(CH$_2$)$_3$COO-2-Ethylhexyl]-3-CH$_3$-6-OH-phenyl (with additional CH$_3$) | 6 |

Examples 24 and 25

0.087 g of the yellow coupler described in Example 11 and a stabilizer indicated in Table 4 are in each case dissolved in 2 ml of a mixture of dibutyl phthalate and ethyl acetate (1.5 g/100 ml). Further processing is as in Example 11.

The resulting colour step wedges are irradiated at a total of 60K joules/cm$^2$ in an Atlas Weather-Ometer behind a UV filter (Kodak 2C) by means of a 2,500 watt xenon lamp, and the losses in colour density are then determined as in Example 11.

The results are collated in Table 4 below.

TABLE 4

| Example | Stabilizer | Loss of colour density, %, at 60 K joules/cm$^2$ |
|---|---|---|
| — | None | 30 |
| 24 | [3,5-(CH$_3$)$_2$-4-OH-phenyl–C(CH$_3$)$_2$(CH$_2$)$_3$COO–CH$_2$–]$_4$C | 13 |

TABLE 4-continued

| Example | Stabilizer | Loss of colour density, %, at 60 K joules/cm² |
|---|---|---|
| 25 |  | 16 |

What is claimed is:

1. A silver halide colour photographic recording material containing at least one blue-green, purple or yellow coupler, which contains, as the stabilizer, a stabilizing amount of at least one compound of the formula I or II

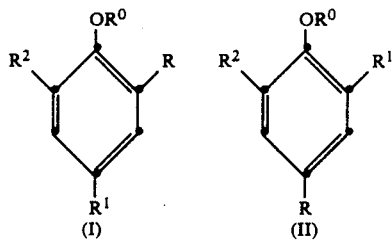

in which R is a group of the formula III or IV

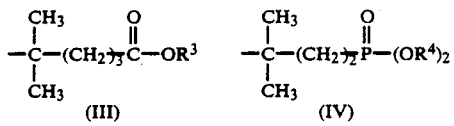

$R^1$ is hydrogen, $C_1$-$C_8$alkyl, cyclohexyl, phenyl-$C_1$-$C_4$alkyl or a group of the formula III or IV, and $R^2$ is as defined for $R^1$, subject to the condition that $R^1$ and $R^2$ cannot simultaneously by hydrogen in the formula II, or $R^2$ is a group of the formula

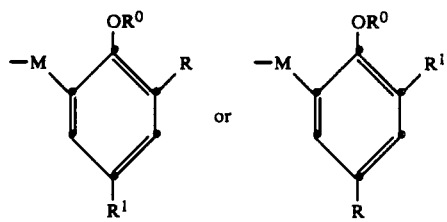

in which M is a direct bond, —$CH_2$— or —S—, $R^3$ is $C_1$-$C_{20}$alkyl which is unsubstituted or substituted by —OH, —$OCOR^5$ or —$OR^5$ and/or which can be interrupted by one or more O atoms, $C_2$-$C_{18}$alkenyl, $C_5$-$C_{12}$cycloalkyl, a phenyl or naphthyl group which is unsubstituted or substituted by one or two alkyl groups, or is phenyl-$C_1$-$C_4$alkyl, a radical (X)— or (X)—$CH_2$— in which (X)— is a member selected from the group consisting of furyl tetrahydrofuran-2-yl, tetrahydropyran-4-yl, methylfuryl, 5-methylfurfur-2-yl and 2,6-dimethyl-tetrahydropyran-4-yl, or is a group of the formula V or VI

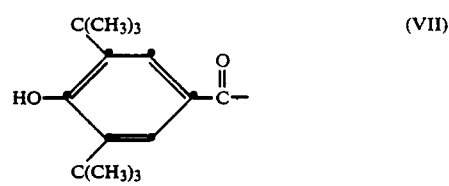

in which n is a number from 1 to 3 and Z is a $C_2$-$C_{18}$alkyl radical which has 2 to 4 valencies and can be interrupted by one or more O and/or S atoms, $R^4$ is $C_1$-$C_{12}$alkyl, $R^5$ is $C_1$-$C_{20}$alkyl, $C_2$-$C_{18}$alkenyl, $C_5$-$C_{12}$cycloalkyl, a phenyl or naphthyl group which is unsubstituted or substituted by one or two alkyl groups, or is phenyl-$C_1$-$C_4$alkyl, $R^0$ is —CO—$R^5$, —CO—$COOR^3$, —Si($R^7$), ($R^8$), $R^9$) or a group of the formula VII, and $R^7$, $R^8$ and $R^9$, independently of one another are $C_1$-$C_4$alkyl, phenyl or benzyl.

2. A composition according to claim 1, wherein $R^3$ in formula III is a radical of the formula V or VI.

* * * * *